United States Patent
Pereira et al.

(10) Patent No.: US 10,888,349 B2
(45) Date of Patent: Jan. 12, 2021

(54) MEDICAL DEVICE HANDLES AND RELATED METHODS

(71) Applicant: Boston Scientific Scimed, Inc., Maple Grove, MN (US)

(72) Inventors: Peter J. Pereira, Mendon, MA (US); David Johnston, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 174 days.

(21) Appl. No.: 15/659,861

(22) Filed: Jul. 26, 2017

(65) Prior Publication Data

US 2018/0028218 A1 Feb. 1, 2018

Related U.S. Application Data

(60) Provisional application No. 62/367,323, filed on Jul. 27, 2016.

(51) Int. Cl.
| | |
|---|---|
| *A61B 17/3205* | (2006.01) |
| *A61B 17/221* | (2006.01) |
| *A61B 17/22* | (2006.01) |
| *A61B 1/00* | (2006.01) |
| *A61B 17/00* | (2006.01) |
| *A61B 17/29* | (2006.01) |

(52) U.S. Cl.
CPC .... *A61B 17/32056* (2013.01); *A61B 1/00133* (2013.01); *A61B 17/221* (2013.01); *A61B 17/22012* (2013.01)

(58) Field of Classification Search
CPC ............ A61B 17/221; A61B 17/32056; A61B 17/2909; A61B 17/29; A61B 2017/2929; A61B 2017/291; A61B 2017/2911; A61B 2017/2912; A61B 2017/2925; A61B 17/22012
See application file for complete search history.

(56) References Cited

U.S. PATENT DOCUMENTS

| | | | |
|---|---|---|---|
| 6,235,026 B1 * | 5/2001 | Smith | ............... A61B 17/2909 606/113 |
| 6,551,327 B1 | 4/2003 | Dhindsa | |
| 6,743,237 B2 | 6/2004 | Dhindsa | |
| 7,294,110 B2 | 11/2007 | Bourne et al. | |
| 7,674,282 B2 | 3/2010 | Wu et al. | |
| 8,021,372 B2 | 9/2011 | Bilitz | |
| 2007/0293874 A1 * | 12/2007 | Okada | ............ A61B 17/320016 606/113 |
| 2009/0112225 A1 * | 4/2009 | Kaneko | ............ A61B 17/32056 606/113 |

(Continued)

*Primary Examiner* — Diane D Yabut
*Assistant Examiner* — Majid Jamialahmadi
(74) *Attorney, Agent, or Firm* — Bookoff McAndrews, PLLC

(57) ABSTRACT

A medical device may include a handle having a first portion and a second portion angled with respect to the first portion. The handle may further include a rail extending along the first portion of the handle. The rail may include a groove. The handle may also include a first actuator longitudinally moveable with respect to the handle along the rail and a second actuator rotatable about an axis collinear to a longitudinal axis of the first portion. Further, the handle may include a shaft longitudinally fixed relative to the first actuator.

17 Claims, 3 Drawing Sheets

(56) References Cited

U.S. PATENT DOCUMENTS

| | | | |
|---|---|---|---|
| 2010/0010512 A1* | 1/2010 | Taylor .................... | A61B 17/04 606/144 |
| 2015/0190159 A1* | 7/2015 | Mark ................. | A61B 17/2909 606/170 |

* cited by examiner

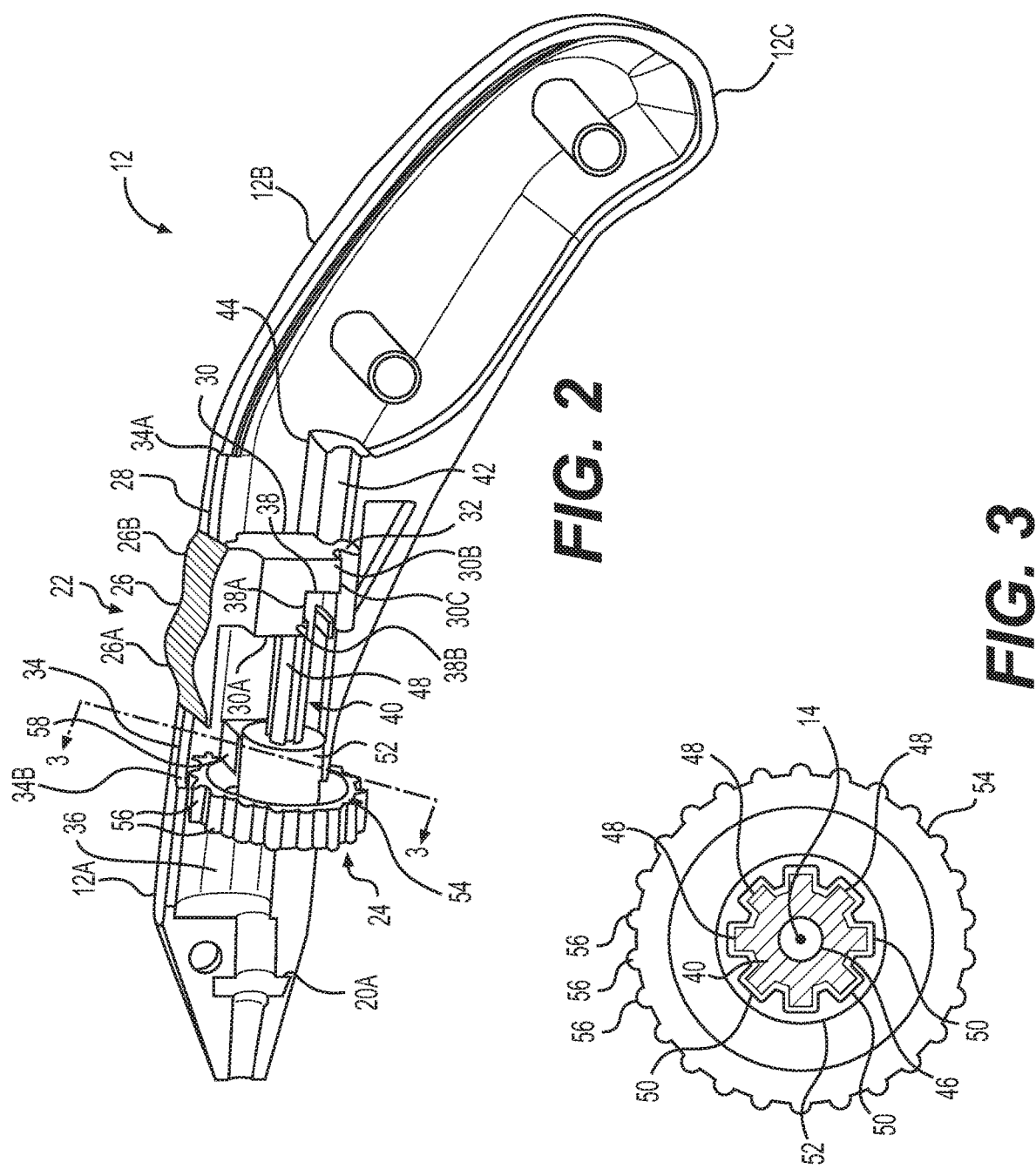

MEDICAL DEVICE HANDLES AND RELATED METHODS

CROSS-REFERENCE TO RELATED APPLICATIONS

This patent application claims the benefit of priority under 35 U.S.C. § 119 to U.S. Provisional Patent Application No. 62/367,323, filed Jul. 27, 2016, which is herein incorporated by reference in its entirety.

TECHNICAL FIELD

Various aspects of the present disclosure relate generally to medical device handles and related methods. More specifically, the present disclosure relates to ergonomic medical device handles for selectively extending, retracting, and/or rotating an end-effector.

BACKGROUND

Retrieval devices, such as baskets, are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Retrieval devices are also used in lithotripsy and ureteroscopy procedures to treat urinary calculi (e.g., kidney stones) in the ureter of a patient.

Current retrieval devices are often cumbersome to operate. For example, handles of current retrieval devices may be awkwardly shaped and/or configured such that manipulation by a user may be functionally and/or intuitively limited. Indeed, handles of such current retrieval devices may fail to prevent inadvertent dislocation of the user's hand with respect to the handle, may require two-hands to extend and retract an end-effector (e.g., basket) of the retrieval devices, and or require forearm rotation to facilitate rotation of the end-effector.

The devices and methods of the current disclosure may rectify some of the deficiencies described above or address other aspects of the prior art.

SUMMARY

Examples of the present disclosure relate to, among other things, medical devices. Each of the examples disclosed herein may include one or more of the features described in connection with any of the other disclosed examples.

In one example, a medical device may include a handle having a first portion and a second portion angled with respect to the first portion. The handle may further include a rail extending along the first portion of the handle. The rail may include a groove. The handle may also include a first actuator longitudinally moveable with respect to the handle along the rail and a second actuator rotatable about an axis collinear to a longitudinal axis of the first portion. Further, the handle may include a shaft longitudinally fixed relative to the first actuator.

Examples of the medical device may include one or more of the following features. The first actuator may include a mount including a curvilinear surface having a first curved portion and a second curved portion. The first curved portion may extend radially outwardly of the handle to a greater extent than the second curved portion. The first actuator may include a main body having a passage therein, the passage may have a first portion with a first radial size and a second portion with a second radial size, and the second radial size may be smaller than the first radial size. The medical device may further include a shaft longitudinally and rotatably fixed with respect to a control member. The shaft may include a plurality of longitudinally extending ribs along an external surface of the shaft. A proximal end of the shaft may be rotatably coupled to a main body of the first actuator. A distal end of the shaft may be longitudinally moveable with respect to a hub of the second actuator. The hub may include an inner surface defining a plurality of channels, wherein each rib of the plurality of ribs may be positioned within a channel of the plurality of channels. A protrusion of the first actuator may be positioned within the groove of the rail. The medical device may further include a longitudinally extending slot positioned on the first portion of the handle. A portion of the first actuator may be received within the longitudinally extending slot. The medical device may further include a slot extending about a portion of the first portion of the handle. A portion of the second actuator may be received within the radially extending slot. The second actuator may be positioned distally of the first actuator.

In a further example, a method may include advancing a first actuator longitudinally along a handle thereby extending an control member coupled to the first actuator relative to a sheath coupled to the handle and moving an extension of the first actuator longitudinally along a groove of a rail of the handle. The method may also include rotating a second actuator about an axis collinear to a longitudinal axis of the control member.

Examples of the method may further include one or more of the following features. Rotating the second actuator may include rotating a shaft fixedly coupled to the control member. Rotating the shaft may include engaging ribs of the shaft with channels of a hub of the second actuator.

In a further example, a medical device may include a handle including a rail having a groove. The medical device may further include a first actuator including an extension received within the groove and longitudinally moveable with respect to the handle. The medical device may further include a second actuator rotatable about an axis collinear to a longitudinal axis of a distal portion of the handle. Additionally, the medical device may include a shaft longitudinally fixed relative to the first actuator.

Examples of the medical device may include one or more of the following features. The second actuator may be positioned distally of the first actuator. The shaft may include a plurality of longitudinally extending ribs. The second actuator may include a hub having an inner surface including a plurality of channels, and each rib of the plurality of longitudinally extending ribs may be positioned within a channel of the plurality of channels. The first actuator may include a mount including a curvilinear surface having a first curved portion and a second curved portion, and the first curved portion extends radially outwardly of the handle to a greater extent than the second curved portion. The handle may include a first portion and a second portion angled with respect to the first portion.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

FIG. 2 illustrates a perspective partial cross-sectional view of the exemplary medical device handle of FIG. 1;

FIG. 3 illustrates a cross-sectional view of a rotatable actuator of the medical device taken along line 3-3 of FIG. 2.

DETAILED DESCRIPTION

Examples of the present disclosure relate to medical device handles for manipulation of an end-effector of the medical device. The medical device may be delivered through any appropriate insertion device, and may include any one or more end-effectors such as, e.g., a basket, a snare, a laser fiber, forceps, a grasper, a probe, scissors, an irrigation and/or aspiration channel, or a needle, etc. Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to an operator using the medical device. In contrast, "distal" refers to a position relatively further away from the operator using the medical device, or closer to the interior of the body.

Figure 1:
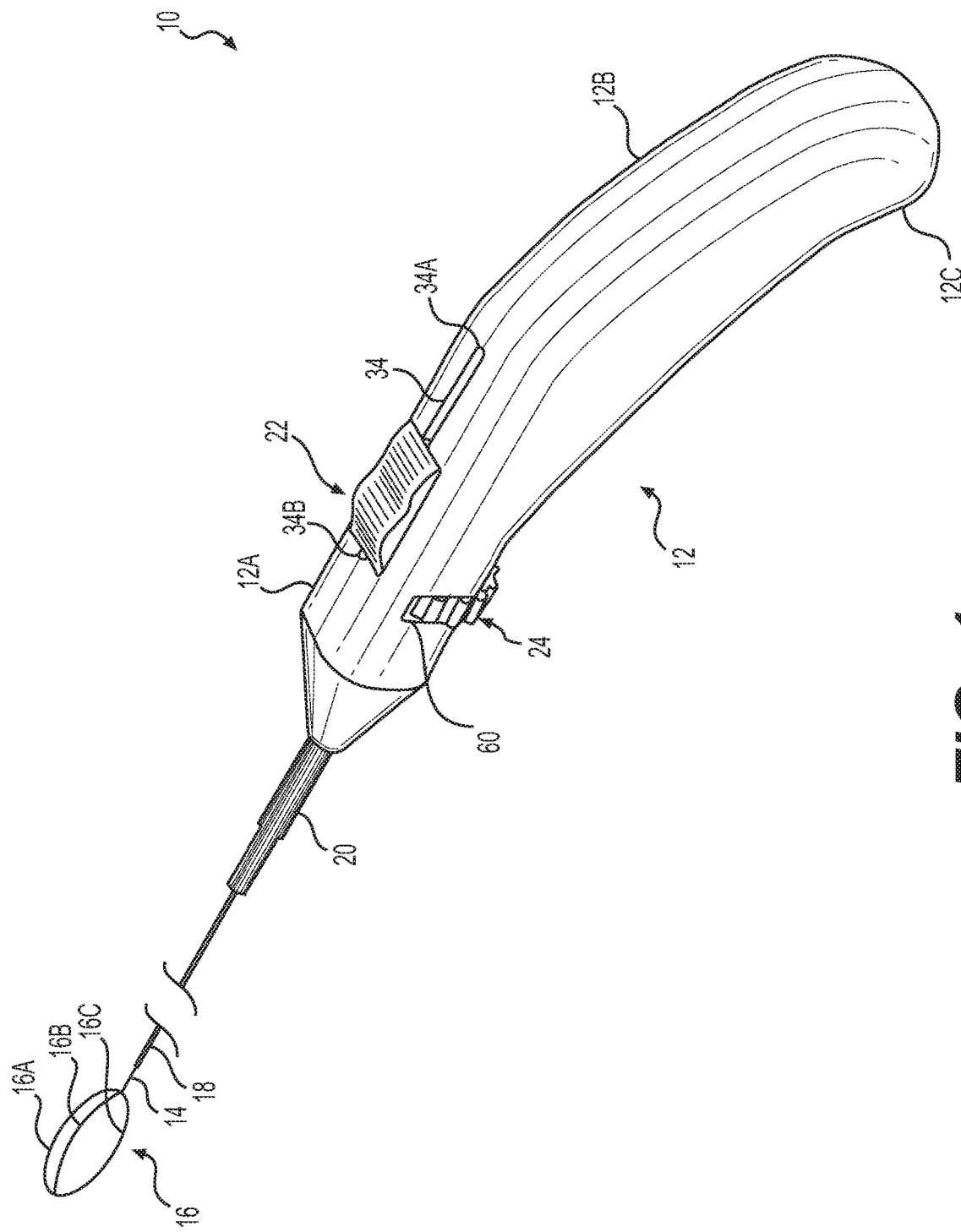
FIG. 1 illustrates an exemplary medical device having a handle and a control member terminating in an end-effector.

FIG. 1 illustrates an exemplary medical device 10, including a handle 12 and an elongate body, wire, shaft, or control member 14 terminating in (e.g., coupled to or monolithically formed with) an end-effector 16, and moveable with respect to a sheath 18. Handle 12 may include a first portion 12A and a second portion 12B. Second portion 12B may be angled with respect to first portion 12A, as described in further detail below. In addition, handle 12 may include a third portion 12C on a proximal end of handle 12, as will be described in further detail below. Handle 12 may be a clam-shell arrangement in which two halves of handle 12 are coupled to one another to form handle 12. Such halves may be coupled together via any appropriate manner known in the art and may optionally be mirror-images of one another.

A distal end of handle 12 may be coupled to a strain-relief member 20. Strain-relief member 20 may have any appropriate shape and arrangement. For example, as shown, strain-relief member 20 may be stepped or tapered in a distal direction. In some arrangements, strain-relief member 20 may be ribbed or otherwise textured. Strain-relief member 20 may comprise any suitable material such as, for example, polymers, rubber, etc., which may flex or bend under applied forces (e.g., bending forces). Strain-relief member 20 may be coupled to a distal end of handle 12 in any appropriate manner. For example, strain-relief member 20 may be retained within handle 12 via a coupling feature located within handle 12, as will be described in further detail below, and may surround, encircle, or otherwise cover a portion (e.g., a proximal portion) of sheath 18 and control member 14. In use, sheath 18 and control member 14 may be bent or angled to facilitate insertion into a subject's anatomy. Strain-relief member 20 may absorb or reduce localized (e.g., concentrated) bending forces applied to sheath 18 and/or control member 14 by spreading such forces along the length of strain-relief member 20. In this manner, kinking of the control member 14 and/or sheath 18 may be avoided.

As noted above, end-effector 16 may include any one or more of a basket, a snare, a laser fiber, forceps, a grasper, a probe, scissors, an irrigation and/or aspiration channel, or a needle, etc. By way of non-limiting example only, end-effector 16 will be depicted and described in reference to a basket hereafter. In use, a medical professional may determine a need or desire to deliver such an end-effector 16 within a subject, to perform a procedure (e.g., to capture a stone or other such material via the basket).

In order to capture a stone or other such material, control member 14 or sheath 18 may be moved relative to the other of control member 14 and sheath 18 to deploy end-effector 16 distally of sheath 18. Accordingly, sheath 18 may be longitudinally fixed with respect to handle 12, while control member 14 may be longitudinally moveable with respect thereto. For example, a proximal end of sheath 18 may be positioned within a lumen (not shown) of strain-relief member 20. Strain-relief member 20 may be heat-shrink coupled, or otherwise fixedly secured around an external surface or wall of sheath 18. Accordingly, sheath 18 is longitudinally fixed with respect to handle 12 via strain-relief member 20.

Control member 14 may extend proximally from end-effector 16 towards handle 12. A proximal end of control member 14 may be coupled to a first actuator 22 of handle 12, as will be described in further detail below. Once coupled, distal advancement or extension of first actuator 22 will cause likewise distal advancement or extension of control member 14 and end-effector 16 relative to sheath 18, as will be described in further detail below. Similarly, proximal retraction or withdrawal of first actuator 22 will cause likewise retraction or withdrawal of control member 14 and end-effector 16 relative to sheath 18, as will be described in further detail below. Once deployed distally of sheath 18, end-effector 16 may transition between a radially collapsed or compressed state toward a radially expanded or uncompressed state. For example, end-effector 16 may be comprised of a self-expandable material (e.g., Nitinol or the like) and upon removal of a radially constraining external force applied by sheath 18, end-effector 16 may automatically assume the radially expanded state, as shown in FIG. 1.

In arrangements in which end-effector 16 includes a basket, as shown, legs 16A, 16B, and 16C may extend radially outwardly of one another so as to "open" end-effector 16. While three legs 16A-16C are shown in FIG. 1, it is understood that any number of legs may be used without departing from the scope of this disclosure. Once in the expanded state, as shown in FIG. 1, the medical professional may manipulate, direct, or otherwise cause legs 16A-16C to capture or retain a stone or other such material therein.

Once extended distally of sheath 18, a medical professional may determine a need or desire to rotate end-effector 16. For example, rotation of end-effector 16 may facilitate positioning a stone or other such material relative to legs 16A-16C of the end-effector 16 to increase ease of capture of such stone or other material within end-effector 16. Additionally or alternatively, rotation of end-effector 16 may enable legs 16A-16C to drag, scrape, or otherwise move along a tissue surface of a subject. Such rotational movement may facilitate removal of stones or other such material within the body of the subject. In order to rotate end-effector 16, control member 14 may be coupled to a second actuator 24 of handle 12, as will be described in further detail below. Second actuator 24 may be rotatable with respect to a portion of handle 12. As such, rotation of second actuator 24 will result in likewise rotation of control member 14, and consequently, end-effector 16, as will be described in further detail below.

FIG. 2 illustrates a perspective partial cross-sectional view of handle 12, illustrating various internal components of handle 12. As noted above, strain-relief member 20 (FIG. 1) may be coupled to handle 12 via a coupling feature 20A located within handle 12. For example, coupling feature 20A may be positioned within a distal portion of first portion 12A of handle 12. Coupling feature 20A may be a recess or other such indentation or groove within which a proximal end of strain-relief member 20 may be received.

As shown in FIG. 2, first actuator 22 may include a thumb or finger mount 26, a neck 28, a body 30, and a protrusion 32. As shown, mount 26 may be ribbed, knurled, or otherwise textured to facilitate secure placement of the medical professional's thumb or finger thereon. In addition, mount 26 may have a curvilinear profile including a first curved portion 26A and a second curved portion 26B, as shown. First curved portion 26A may extend radially outwardly of handle 12 to a greater extent than second curved portion 26B. The first and second curved portions 26A and 26B may facilitate manipulation of the first actuator 22 via a thumb or finger of the medical professional. For instance, the medical professional may position his/her thumb or finger between first curved portion 26A and second curved portion 26B. As such, during distal advancement of first actuator 22, the medical professional may apply a push force on first curved portion 26A. Additionally, during proximal retraction of first actuator 22, the medical professional may apply a pull force on second curved portion 26B. As such, first and second curved portions 26A and 26B may provide increased leverage to a medical professional during actuation (e.g., extension and/or retraction) of first actuator 22.

As shown, mount 26 may be coupled to body 30 via neck 28. Neck 28 may be thinned or narrowed relative to mount 26 and body 30. That is, neck 28 may have a width smaller than mount 26 and body 30. As such, neck 28 may be received within a channel or slot 34 extending through handle 12. For example, as shown in FIGS. 1 and 2, slot 34 may extend through an upper, outer circumferential surface of first portion 12A of handle 12. Slot 34 may define a maximum stroke length of first actuator 22, and therefore, a maximum distance control member 14 may move with respect to sheath 18. In other words, a proximal end 34A and a distal end 34B of slot 34 may be proximal and distal stops of first actuator 22, respectively. Upon assembling handle 12, body 30 may remain within a central chamber 36 of handle 12, while mount 26 may be positioned exterior of central chamber 36. In such a manner, neck 28 may straddle or span the radial thickness of slot 34, while body 30 and mount 26 prevent inadvertent removal of first actuator 22 from handle 12.

Body 30 may include an opening or passage 38 arranged for receipt of a shaft 40, as will be described in further detail below. Passage 38 may extend through multiple faces or surfaces of body 30. For instance, passage 38 may extend through a distal-facing surface 30A, through a lateral surface 30B, and through a bottom or downward-facing surface 30C of body 30. In addition, passage 30 may have a varied profile. That is, a first portion 38A of passage 38 may have a first diameter or dimension, while a second portion 38B of passage 30 may have a second diameter or dimension smaller (e.g., more narrow) than the first diameter or dimension. In other words, second portion 38B may include an inwardly projecting extension, rim, or tab thereby narrowing a portion (e.g., a distal portion) of passage 38.

Protrusion 32 may depend downwardly from downward-facing surface 30C of body 30. Protrusion 32 may have any appropriate shape so as to mate or correspond with a complimentary shaped channel or groove 42 of a rail 44. For example, as shown in FIG. 2, protrusion 32 may have an ovular or rounded cross-sectional shape. In addition, groove 42 may be rounded, curvilinear, or otherwise complimentary (e.g., matching, corresponding, etc.) in shape to protrusion 32. In such a manner, protrusion 32 may be retained within groove 42, as will be described in further detail below. While groove 42 and protrusion 32 are described and depicted as curved, the disclosure is not so limited. Rather, any complimentary shaped surfaces may be used to form a similar dovetail type arrangement in which protrusion 32 is received within groove 42. It is understood that while a single rail 44 is illustrated, each clam-shell half of handle 12 may have a rail 44 which may cooperate in conjunction with one another to secure protrusion 32 therein.

As noted above, body 30 includes passage 38 for receipt of shaft 40. As shown in FIG. 3, shaft 40 may include a central lumen 46 extending longitudinally therethrough. Control member 14 may extend through lumen 46 and may be fixed to an inner circumferential surface of lumen 46 via any appropriate manner (e.g., heat staking, adhesives, mechanical fasters, etc., not shown). Accordingly, advancement, retraction, and rotation, of shaft 40 may result in likewise advancement, retraction, and rotation, respectively, of control member 14, and consequently, end-effector 16. In addition, a radially exterior surface of shaft 40, may be fluted or otherwise ribbed. That is, as shown in FIGS. 2 and 3, the radially exterior surface of shaft 40 may include a plurality of ribs 48. While eight equidistantly spaced ribs 48 are depicted in FIG. 3, the disclosure is not so limited. Rather, any appropriate number of ribs 48 (e.g., between about 2 and about 20) may be arranged about the radially exterior surface of shaft 40 in either an equidistantly or non-equidistantly spaced pattern without departing from the scope of this disclosure.

Each rib 48 may be aligned with a corresponding channel 50 on an interior surface of a hub 52 of second actuator 24. Hub 52 may have any number and arrangement of channels 50 corresponding to the number and arrangement of ribs 48. As shown, each rib 48 may be received within a channel 50 of with clearance therebetween. That is, a small space or gap is provided between adjacent surfaces of ribs 48 and channels 50. Such clearance enables shaft 40 to move (e.g., advance, retract, slide, translate, etc.) with respect to hub 52 of second actuator 24 (e.g., into and out of the page with respect to FIG. 3). In other words, actuation of first actuator 22 to extend end-effector 16 may cause shaft 40, to extend through hub 52 of second actuator 24. However, due to interaction between ribs 48 and channels 50 of hub 52, rotation of hub 52 will result in likewise rotation of shaft 40, which will result in rotation of control member 14 due to the coupling of control member 14 to shaft 40. For example, as shown in FIGS. 2 and 3, hub 52 may be coupled to or monolithically formed with a wheel extension 54. As shown, wheel extension 54 may be a circular member and may be rotatable about an axis parallel with a longitudinal axis of first portion 12A of handle 12. For example, wheel extension 54 may be rotatable about a longitudinal axis of control member 14 within first portion 12A of handle 12 and may extend through a slot 60 (FIG. 1) cut or otherwise formed in handle 12. Wheel extension 54 may be arranged perpendicular to sheath 18 and may include a ribbed, raised, or otherwise textured surface. For example, wheel extension 54 may have a radially outer surface including a plurality of grips or ribs 56 to facilitate secure manipulation by a medical professional. Accordingly, in use, a medical professional may place a finger or thumb on wheel extension 54.

Upon rotation of wheel extension 54, hub 52 will also rotate. Further, rotation of hub 52 will result in likewise rotation of shaft 40 due to interference between channels 50 and ribs 48. Finally, rotation of shaft 40 will result in rotation of control member 14 and end-effector 16 due to the connection of control member 14 to shaft 40. As shown in FIG. 2, handle 12 may further include an alignment support 58. For example, alignment support 58 may be coupled to each half of handle 12 so as to minimize movement of hub 52 radially outward of the longitudinal axis of control member 14 and shaft 40, thereby preventing unnecessary friction between hub 52 and shaft 40.

Figure 4:
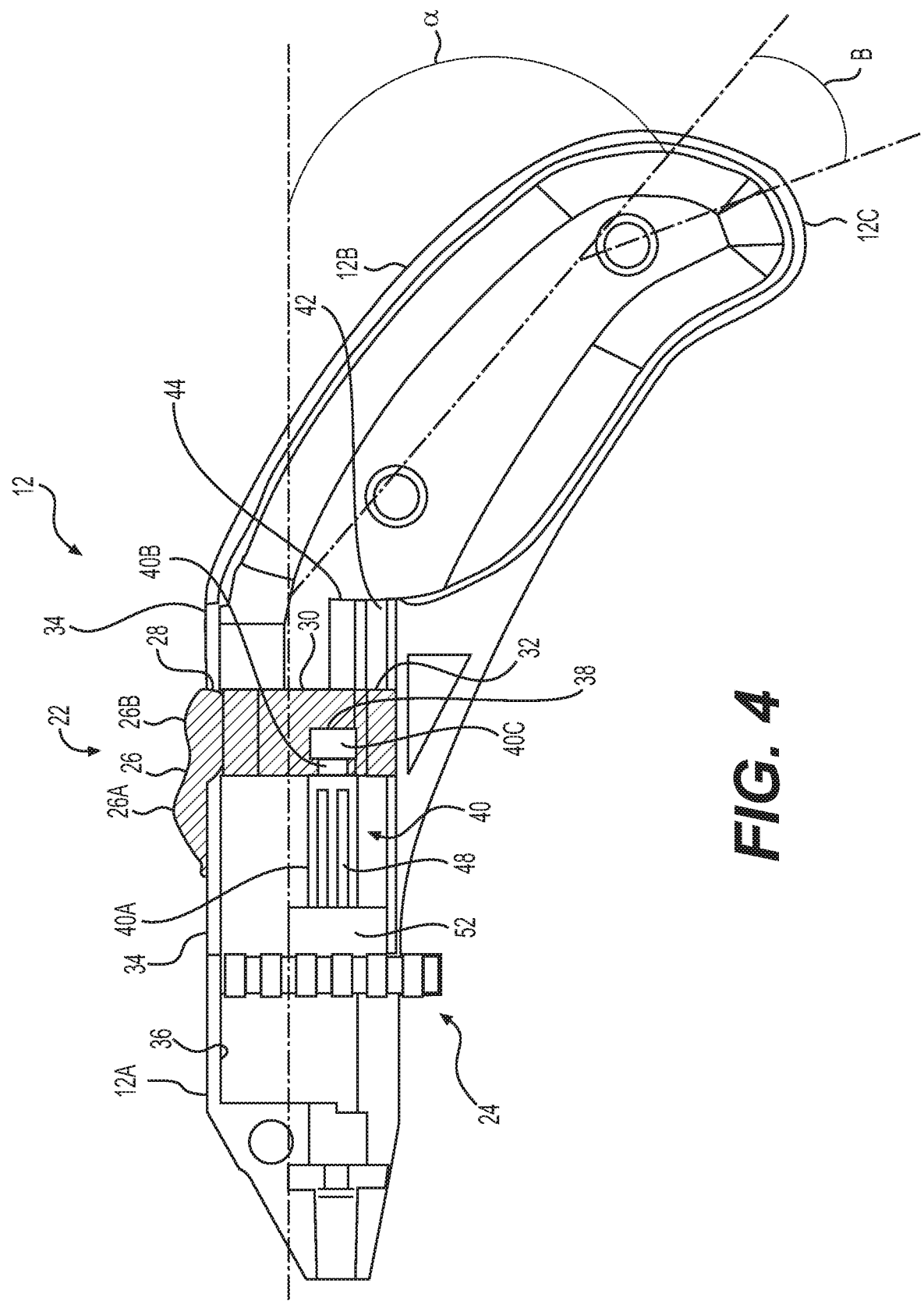
FIG. 4 illustrates a partial cross-sectional side-view of the exemplary medical device handle of FIG. 1.

FIG. 4 illustrates a partial cross-sectional side-view of the exemplary medical device handle of FIG. 1. As shown in FIG. 4, shaft 40 includes a main body portion 40A, a neck portion 40B, and a shaft hub 40C. Upon coupling, hub 40C may be located within first portion 38A (FIG. 3) of passage 38, while neck portion 40B may be received within second portion 38B (FIG. 3) of passage 38. Additionally, while main body portion 40A includes ribs 48, as discussed above, neck portion 40B and shaft hub 40C must not include such ribs 48. That is, neck portion 40B and shaft hub 40C may be smooth surfaces to facilitate rotation of shaft 40 with respect to body 30 of first actuator 22.

Additionally, as noted above, handle 12 includes first portion 12A, second portion 12B, and third portion 12C. As shown in FIG. 4, first portion 12A may extend along a longitudinal axis of control member 14 while second portion 12B may be angled with respect to first portion 12A. For example, second portion 12B may extend at an angle α of about 45° with respect to first portion 12A. For example, angle α may be between about 20° and about 60°, between about 30° and about 50°, or between about 40° and about 50°. Meanwhile, third portion 12C may be angled with respect to second portion 12B. For example, third portion 12C may extend at an angle β of about 30° with respect to second portion 12B. For example, angle β may be between about 20° and about 40°, between about 25° and about 35°, or between about 28° and about 32°. Such an angled arrangement of handle 12 may facilitate ergonomic gripping of handle 12. As handle 12 is symmetric about a longitudinal axis of control member 14, the medical professional may hold handle 12 in either hand (e.g., the right or left hand) depending on their own personal preference. Intuitively, the medical professional will grip handle 12 such that their thumb will be positioned on first actuator 22 while the middle, ring, and pinky finger will wrap around handle 12. Naturally, the index finger of the medical professional may be mobile to either rest next to the middle finger or on the second actuator 24. In such a way, handle 12 enable single-handed intuitive control of end-effector 16.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical device, comprising:
   a handle having a first portion and a second portion angled with respect to the first portion;
   a control member having a proximal end located within the handle and a distal end terminating in an end-effector;
   a rail extending along the first portion of the handle, the rail including a groove;
   a first actuator longitudinally moveable with respect to the handle along the rail;
   a second actuator rotatable about a central axis parallel to a central longitudinal axis of the first portion; and
   a shaft longitudinally fixed relative to the first actuator and including a plurality of longitudinally extending ribs along an external surface of the shaft, wherein the proximal end of the control member is received within a lumen of the shaft and is fixed relative to the shaft for movement therewith.

2. The medical device of claim 1, wherein the first actuator includes a mount including a curvilinear surface having a first curved portion and a second curved portion.

3. The medical device of claim 2, wherein the first curved portion extends radially outwardly of the handle to a greater extent than the second curved portion.

4. The medical device of claim 1, wherein the first actuator includes a main body having a passage therein, wherein the passage has a first portion with a first radial size and a second portion with a second radial size, wherein the second radial size is smaller than the first radial size.

5. The medical device of claim 1, wherein a proximal end of the shaft is rotatably coupled to a main body of the first actuator.

6. The medical device of claim 5, wherein a distal end of the shaft is longitudinally moveable with respect to a hub of the second actuator.

7. The medical device of claim 6, wherein the hub includes an inner surface defining a plurality of channels, wherein each rib of the plurality of ribs is positioned within a channel of the plurality of channels.

8. The medical device of claim 1, wherein a protrusion of the first actuator is positioned within the groove of the rail.

9. The medical device of claim 1, wherein the second actuator is positioned distally of the first actuator.

10. A medical device, including:
    a handle including a rail having a groove;
    a control member terminating in an end-effector;
    a first actuator including an extension received within the groove and longitudinally moveable with respect to the handle;
    a second actuator rotatable about a central axis parallel to a central longitudinal axis of a distal portion of the handle; and a shaft longitudinally fixed relative to the first actuator, a proximal end of the control member being coupled to the shaft, and the shaft including a varied cross-sectional dimension so as to define a neck portion, wherein the neck portion of the shaft is retained within a passage of a main body of the first actuator via a retaining extension of the main body for longitudinal movement with the first actuator, and wherein the shaft includes a plurality of longitudinally extending ribs.

11. The medical device of claim 10, wherein the second actuator is positioned distally of the first actuator.

12. The medical device of claim 10, wherein the second actuator includes a hub having an inner surface including a plurality of channels, wherein each rib of the plurality of longitudinally extending ribs is positioned within a channel of the plurality of channels.

13. The medical device of claim 10, wherein the first actuator includes a mount including a curvilinear surface having a first curved portion and a second curved portion, wherein the first curved portion extends radially outwardly of the handle to a greater extent than the second curved portion.

14. The medical device of claim 13, wherein the handle includes a first portion and a second portion angled with respect to the first portion, wherein each of the first actuator and the second actuator are located along the first portion of the handle.

15. A medical device, comprising:
a handle having a first portion and a second portion angled with respect to the first portion;
a control member having a proximal end located within the handle and a distal end terminating in an end-effector;
a first actuator longitudinally moveable with respect to the handle and positioned along the first portion of the handle, wherein the first actuator includes a main body having a passage therein, wherein the passage has a first passage portion with a first radial size and a second passage portion with a second radial size, wherein the second radial size is smaller than the first radial size;
a second actuator rotatable about a central axis parallel to a central longitudinal axis of the first portion and positioned along the first portion of the handle; and
a shaft longitudinally fixed relative to the first actuator, wherein the proximal end of the control member is fixed relative to the shaft for movement therewith.

16. The medical device of claim 15, wherein a distal end of the shaft is longitudinally moveable with respect to a hub of the second actuator.

17. The medical device of claim 6, wherein the hub includes an inner surface defining a plurality of channels and the shaft includes a plurality of longitudinally extending ribs along an external surface of the shaft, wherein each rib of the plurality of ribs is positioned within a channel of the plurality of channels.

* * * * *